United States Patent [19]
Weimer

[11] Patent Number: 5,998,222
[45] Date of Patent: *Dec. 7, 1999

[54] RECONDITIONING ANTIBIOTIC-ADULTERATED MILK PRODUCTS

[75] Inventor: Bart C. Weimer, Logan, Utah

[73] Assignee: Utah State University, Logan, Utah

[ * ] Notice: This patent is subject to a terminal disclaimer.

[21] Appl. No.: 08/424,785

[22] Filed: Apr. 19, 1995

Related U.S. Application Data

[63] Continuation-in-part of application No. 08/159,379, Nov. 29, 1993, abandoned.

[51] Int. Cl.⁶ .............................. G01N 33/543; A23P 1/00
[52] U.S. Cl. .................... 436/518; 436/524; 436/527; 436/528; 436/531; 436/23; 530/413; 426/665; 426/422; 426/271
[58] Field of Search ............................ 436/518, 524–527, 436/528, 531, 536, 538, 541, 548, 20, 22, 23; 530/412, 413; 435/7.1, 7.21, 7.32; 426/422, 665, 286, 271, 330, 330.8, 335

[56] References Cited

U.S. PATENT DOCUMENTS

| | | |
|---|---|---|
| 4,238,521 | 12/1980 | Charm . |
| 4,347,312 | 8/1982 | Brown et al. . |
| 4,589,927 | 5/1986 | Allen et al. . |
| 4,639,513 | 1/1987 | Hou et al. . |
| 4,687,820 | 8/1987 | Hou et al. . |
| 4,840,895 | 6/1989 | Self . |
| 5,077,210 | 12/1991 | Eigler et al. . |
| 5,310,565 | 5/1994 | Geyer . |

OTHER PUBLICATIONS

S.K. Bhatia et al. Use of Thiol–Terminal Silanes and Heterobifunctional Crosslinkers for Immobilization of Antibodies on Silica Surfaces, Anal. Biochem. 178:408–413, 1989.

Ho et al. Journal of Food Science vol. 55 #44, 1990 1172–1173 "Purification of Milk Catalace . . . "

Voller et al, *Immunoassays for the 80s,* 1981 p.77.

Pharmacia Affinity Chromatography Principles & Methods 1986 pp. 83–89.

Skjerve et al. "Detection of Listeria Monocytogens . . . " Applied an Environmental Microbiology vol. 56, #11, Nov. 1990 pp. 3478–3481.

Van De Water et al. "A Sensitive Streptaindin–Biotin . . . " Food and Agricultural Immunology vol. 2 1990 pp. 11–19.

Comparisons of On–Farm Screening Tests for Detection of Antibiotic Residues by, E.H. Seymour, G.M. Jones and M.L. McGilliard, 1992.

*Primary Examiner*—Patricia Duffy
*Attorney, Agent, or Firm*—Thorpe, North & Western, L.L.P.

[57] ABSTRACT

A method for removing a selected contaminant from a liquid food product is disclosed. A special application of the method is for removing an antibiotic from milk. The method comprises the steps of contacting the milk with a matrix-antibody composition, wherein the antibody has a specific affinity for the selected contaminant, for a time and at a temperature sufficient for the contaminant to bind to the antibody to form a complex, and separating the complex from the food product. The matrix-antibody composition is regenerable by treating the complex with high ionic strength solution to release bound contaminants from the antibodies.

33 Claims, 2 Drawing Sheets

RECONDITIONING ANTIBIOTIC-ADULTERATED MILK PRODUCTS

This is a continuation-in-part of application Ser. No. 08/159,379, filed Nov. 29, 1993, abandoned.

BACKGROUND OF THE INVENTION

This invention relates generally to food products that have been adulterated with antibiotics or other contaminants. More particularly, this invention relates to a method for reconditioning dairy products, especially milk, that have been adulterated with antibiotics or other contaminants.

Antibiotics have greatly improved the quality and duration of life because they kill or inhibit growth of primarily prokaryotic microorganisms, many of which are disease-causing agents. In addition to their use in human medicine, antibiotics are also administered to livestock at therapeutic, prophylactic, or sub-therapeutic levels. S. Levy, 50 J. Food Prot. 616 (1987). Therapeutic administration is for disease treatment, prophylactic administration is to prevent disease, and sub-therapeutic administration is for increasing feed efficiency and promoting growth. In 1983, nearly one-half of the 35 million pounds of antibiotics manufactured in the U.S. was fed to animals. W. Tindall, 40 Animal Nutrition and Health 18 (1985). The cattle, swine, and poultry industries are the largest users of antibiotics, particularly penicillins and tetracyclines. C. Burbee et al., Am. J. Agr. Econ. 966 (1985). The administration of antibiotics to animals has become so widespread that nearly 80% of poultry, 75% of swine, 60% of feed lot cattle, and 75% of dairy calves are fed antibiotics. D. Franco et al., 53 J. Food Prot. 178 (1990).

Bacteria can become resistant to antibiotics, and this resistance can occur in a short period of time after therapeutic or sub-therapeutic exposure. Therapeutic oral intake of tetracycline in humans can lead to emergence of a predominantly tetracycline-resistant coliform gastrointestinal flora within 48 hours. L. Hartley & M. Richmond, 4 Brit. J. Med. 71 (1975). Sub-therapeutic levels of tylosin fed to piglets led to 100% macrolide-resistant fecal streptococci within a few days. G. Dunny et al., Effects of Antibiotics in Animal Feed on the Antibiotic Resistance of the Gram Positive Flora of Animals and Man (New York Public Health Inst. 1978).

Antibiotic resistance in microorganisms can be transferred to other organisms, generally on plasmids. These plasmids often carry multiple drug resistance genes, thus administration of antibiotics develops resistance not only to the antibiotic being administered but to other antibiotics as well. Humans may become infected with antibiotic-resistant microorganisms by consuming meat, milk, or other animal products from animals in which the microorganisms have developed. S. Holmberg et al., 311 N. Engl. J. Med. 617 (1984); C. Ryan et al., 258 J. Am. Med. Ass'n 3269 (1987). Ironically, the humans at greatest risk may be those taking antibiotics for treatment of other conditions. S. Holmberg et al., 311 N. Engl. J. Med. 617 (1984). The Center for Disease Control estimates that 25% of the Salmonella isolated from human infections are resistant to antibiotics.

After reviewing data on drug resistance-plasmid transfer, the Food and Drug Administration (FDA) began regulating use of antibiotics in animals destined for human consumption. As of July, 1991, 23 antimicrobial agents were FDA-approved for one or more uses in livestock and poultry feeds. 33 Food Chem. News 51 (1991). The FDA requires specific withdrawal times after treatment with antibiotics for livestock prior to lactation or slaughter. For example, FDA regulations require that milk from treated cows be discarded for 96 hours following the last administration of the antibiotic. E. Seymour et al., 71 J. Dairy Sci. 2792 (1988). Further, the FDA establishes tolerance limits, the maximum legally allowable levels or concentrations of a drug or chemical in a food product at the time the milk is marketed or the animal is slaughtered. "Safe levels" are also used by the FDA as guides for deciding whether or not to prosecute. They are not binding, do not dictate any result, do not limit the FDA's discretion in any way, and do not protect milk producers from court enforcement action. For some antimicrobials, no tolerance or safe level is allowed. 21 C.F.R. § 556 (1993).

In 1991, the FDA began the National Drug Residue Milk Monitoring Program to test for various drug residues in milk. A requirement under the Pasteurized Milk Ordinance (PMO) for industry screening of all bulk milk pickup containers for β-lactam antibiotic residues went into effect Jan. 1, 1992. Pasteurized Milk Ordinance, Appendix N. Further, tankers are randomly tested for the presence of other drug residues in milk, and all test results are reported to the appropriate state regulatory agency. Upon a first violation of the regulation, Grade A permits (for fluid milk) are revoked for 2 days. Upon a second violation, Grade A permits are revoked for 4 days, and upon a third violation the permit may be suspended. Pasteurized Milk Ordinance, Appendix N.

In 1993, the U.S. Department of Agriculture (USDA) instituted a drug residue monitoring program for manufacturing grade milk. This program requires that all USDA-approved dairy plants sample and test all raw milk shipments individually for β-lactam drugs prior to processing. Further, each violative producer will be reported to the appropriate state regulatory agency by the plant and will be suspended from shipment until milk from subsequent milkings tests negative for drug residues. Besides nonacceptance of milk containing drug residues, additional penalties are provided for producers who ship milk testing positive for drug residues.

A survey conducted by the Milk Industry Foundation, representing 78% of the total volume of fluid Grade A milk in 1992, revealed that 1,770 tankers of milk, or about 0.09% of the total, tested positive for drug residues. Of that total, about 90% were β-lactams, 4% were tetracyclines, 4% were sulfamethazine, 2% were erythromycin, and 0.2% were gentamicin. While the percentage of contaminated tankers was relatively low, individual producers may suffer significant economic effects from having antibiotics detected in their milk. The reasons for occurrence of drug residues in milk is mainly associated with errors due to hired help, insufficient knowledge about withdrawal periods, poor animal identification techniques and documentation of treated animals, and the use of medicated feeds. J. Kaneene & A. Ahl, 70 J. Dairy Sci. 2176 (1987). The PMO provides that antibiotic-adulterated milk may be reconditioned by removal of the offending antibiotics from the milk, Pasteurized Milk Ordinance, Appendix N, however there is currently no economically viable commercial method to accomplish it.

Other types of contaminants can also adulterate milk and other liquid food products, and it is desirable to remove such contaminants therefrom. Such contaminants can include bacterial cells, bacterial spores, viruses, proteins, and enzymes. Commercial methods to remove such contaminants without altering the natural composition of the milk or other liquid food product are unknown in the art.

R. Brown et al., U.S. Pat. No. 4,347,312, disclose a method akin to radioimmunoassay (RIA) for detecting the presence of penicillin in milk. Anti-penicillin antibodies are bound to a solid support. Then, a milk sample is mixed with a known quantity of horseradish peroxidase-labeled penicillin and exposed to the support. Alternatively, the support is exposed to the milk sample and the labeled penicillin consecutively. The support is rinsed and then the amount of labeled penicillin bound to the support is determined with a calorimetric substrate. Penicillin in the milk sample and the labeled penicillin compete for attachment to bound antibodies, thus the amount of penicillin in the milk sample can be determined by comparison to a standard curve. This method is effective for quantifying an antibiotic in a small, static volume of milk, but is ineffective for quantitative removal of contaminants on an industrial scale wherein an immobilized antibody is exposed to the high shear forces associated with the high flow rates of an industrial process. Also, the solid support and associated antibodies are discarded after one use, thus making the method expensive. Further, the immobilized antibody is nonspecifically oriented on the solid support such that only one antigen binding site per antibody is available for binding an antigen in milk.

Charm, U.S. Pat. No. 4,238,521, discloses a method of removing penicillin from penicillin-contaminated milk comprising the steps of contacting the penicillin-contaminated milk with a bed of activated charcoal, recycling the milk through the bed of charcoal for a sufficient period to remove the penicillin from the contaminated milk to provide a penicillin-free milk, removing particulate activated charcoal acquired during the contacting step by filtration and centrifugation, and recovering the penicillin-free milk. This method is a crude, shotgun approach and provides no specificity for removing any particular constituent of the penicillin-contaminated milk. Indeed, normal components of milk are removed by contacting the milk with activated charcoal. Further, charcoal particles contaminate the milk after being contacted by the activated charcoal, and steps must be taken to remove such particles from the penicillin-free milk. Moreover, the method is relatively slow, and the capacity for removing antibiotics is relatively low, which are disadvantages compared to the presently disclosed invention.

R. Geyer, U.S. Pat. No. 5,310,565, discloses a method of treating milk to remove antibiotics comprising heating the antibiotic-contaminated milk to a temperature sufficient to solubilize fats, contacting the heated milk with an ion exchange or adsorbent resin to produce an antibiotic-depleted milk, and collecting the antibiotic-depleted milk. This method is also relatively crude and non-specific as shown by altered mineral profiles, removal of proteins such as riboflavin, and altered pH of the antibiotic-depleted milk. These changes are also disadvantages as compared to the presently disclosed invention.

In view of the foregoing, it will be appreciated that a method for specifically removing a selected contaminant, such as an antibiotic, bacterial cell, bacterial spore, virus, enzyme, or protein, from milk or other liquid food product without altering the natural composition of the milk or other liquid food product would be a significant advancement in the art.

OBJECTS AND SUMMARY OF THE INVENTION

An object of the present invention is to provide a method for reconditioning a contaminant-adulterated liquid food product by removing a contaminant in the liquid food product.

Another object of the invention is to provide a method that can be used on an industrial scale for removing contaminants from a liquid food product, such as an antibiotic in milk.

It is also an object of the invention to provide a quick, efficient, and inexpensive method for removing a contaminant from a liquid food product.

Still another object of the invention is to provide a reusable system for removing a contaminant from a liquid food product.

These and other objects can be accomplished by providing a method for removing a selected contaminant from contaminated milk comprising the steps of:

(a) providing a matrix-antibody composition comprising an insoluble matrix having an antibody bonded thereto, the antibody having a specific affinity for binding the selected contaminant;

(b) contacting the contaminated milk with an effective amount of the matrix-antibody composition for a time and at a temperature sufficient for the contaminant to form a complex with said matrix-antibody composition, thereby forming contaminant-depleted milk; and (c) separating the complex from the contaminant-depleted milk.

The selected contaminant can be an antibiotic, bacterial cell, bacterial spore, virus, protein, enzyme, or the like. A special application of this method is for removing an antibiotic from antibiotic-contaminated milk. Preferred antibiotics that can be removed from milk with this method include β-lactam antibiotics, such as penicillin, and gentamicin. Preferred matrix materials include silicon, glass, silica, quartz, metal oxides including certain ceramic materials, polyvinyl alcohol, polystyrene, and poly(acrylic acid), with glass, ceramic, and polystyrene being more preferred. It is also preferred that the matrix is in the form of a bead, preferably with a diameter in the range of about 2–7 mm. It is preferred to directionally attach the antibody to the matrix such that the antibody has multiple antigen binding sites available for forming a complex with the selected contaminant.

Another aspect of the invention is that the matrix-antibody composition is reusable after removal of the contaminant from the complex. Treatment of the complex with high ionic strength solutions, for example high concentrations of salt, releases the contaminant without impairing the avidity of the matrix-bound antibody for subsequent affinity reactions.

DETAILED DESCRIPTION OF THE INVENTION

Figure 1:
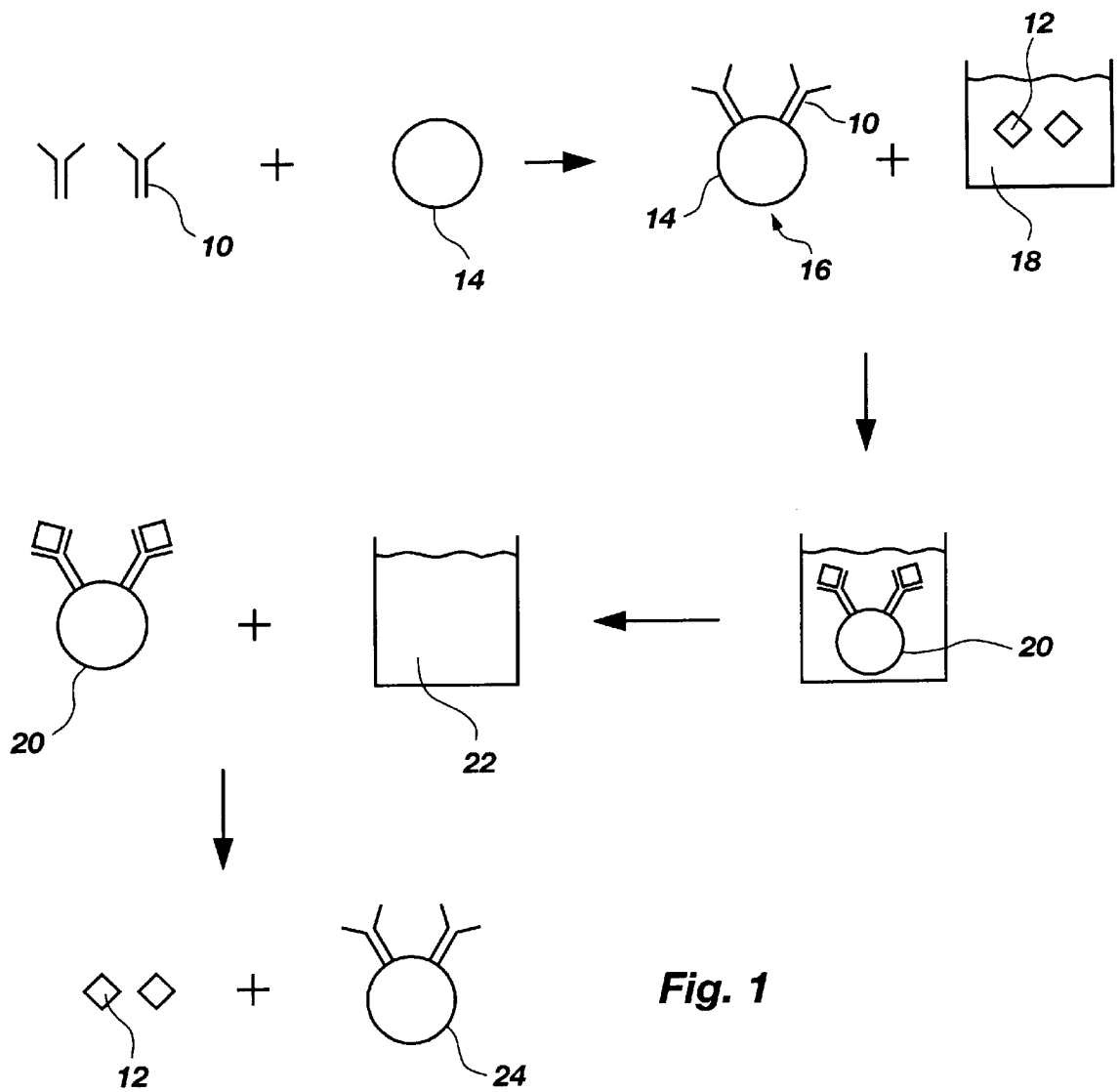
FIG. 1 is a schematic diagram of the method of reconditioning antibiotic-adulterated food products according to the present invention.

Before the present method of reconditioning antibiotic-adulterated milk or other contaminated liquid food products is disclosed and described, it is to be understood that this invention is not limited to the particular process steps and materials disclosed herein as such process steps and materials may vary somewhat. It is also to be understood that the terminology employed herein is used for the purpose of describing particular embodiments only and is not intended to be limiting since the scope of the present invention will be limited only by the appended claims and functional equivalents thereof.

It must be noted that, as used in this specification and the appended claims, the singular forms "a," "an," and "the" include plural referents unless the context clearly dictates otherwise. Thus, for example, reference to a solid matrix containing "an antibody" includes a mixture of two or more antibodies, reference to "a contaminant" includes reference to one or more of such contaminants, and reference to "a cross linker" includes reference to a mixture of two or more cross linkers.

In describing and claiming the present invention, the following terminology will be used in accordance with the definitions set out below.

As used herein, "liquid food product" means an ingestible liquid that contains nutritional value. Exemplary liquid food products include milk, fruit juice and other beverages, and broth. A preferred liquid food product is milk. The term "milk" is meant to include raw milk, cream, low fat or reduced fat milk, nonfat milk, and the like that is used as a food by humans, regardless of the animal of origin. Cow's milk is preferred, however.

As used herein, "matrix" means an insoluble solid support that is compatible both with binding of an antibody and for contacting a liquid food product such as milk. Such matrix should be composed of a material containing functional groups, or that can be derivatized to contain functional groups, for binding of an antibody. Preferred matrix materials are inorganic materials including but not limited to silicon, glass, silica, quartz, and metal oxides such as certain ceramic materials, as well as organic polymers such as polyvinyl alcohol, polystyrene, and acrylic acid polymers. Ceramic materials composed of metal oxides are more preferred.

As used herein, "matrix-antibody composition" means a matrix to which an antibody has been bound such that the antibody is immunologically active, i.e. the antibody remains capable of specifically binding an antigen by the well known antigen-antibody binding reaction. It is preferred that the binding of the antibody to the matrix is by "directional attachment," i.e. the antibody is bound to the matrix such that multiple antigen binding sites of the antibody remain available for binding an antigen, such as an antibiotic. Directional attachment is to be distinguished from "nonspecific attachment" wherein one of the antigen binding sites of an antibody is used to attach such antibody to a solid support, thus leaving only one antigen binding site available for binding an antigen, such as an antibiotic, in the liquid food product. While both directional and nonspecific attachment are considered within the scope of the invention, directional attachment is preferred.

As used herein, "complex" means the product of an antibody and an antigen bound together by a specific antigen-antibody binding reaction, i.e. an antigen-antibody complex.

As used herein, "high ionic strength solution" means a solution with sufficiently high ionic strength to cause the breaking of an antigen-antibody complex such that the antibody and antigen are no longer bound together by a specific antibody-antigen binding reaction. Thus, a high ionic strength solution is to be limited only by functionality. The concentration of solute needed for breaking any particular antibody-antigen complex will depend on the association constant of the antigen and antibody. For example, most antibodies have association constants in the range of $10^5$–$10^9$ liters/mole. Very strong binding, however, in the range of $10^{10}$–$10^{12}$ liters/mole has been reported. Exemplary high ionic strength solutions include 0.5 to 2 M NaCl, KCl, or $MgCl_2$ solutions, and 0.5 to 1 M NaCl is preferred.

As used herein, "antibiotic" means a drug that is administered to inhibit the growth of or kill an microorganism in a milk-producing mammal. Antibiotics for which tolerance or safe levels have been established for cow's milk include amoxicillin, ampicillin, bacitracin, ceftiofur, cephapirin, chlortetracycline, cloxacillin, dihydrostreptomycin, erythromycin, gentamicin, lincomycin, neomycin, novobiocin, oxytetracycline, penicillin, sulfachlorpyridazine, sulfadiazine, sulfadimethoxine, sulfamerazine, sulfamethazine, sulfamethizole, sulfanilamide, sulfapyridine, sulfathiazole, tetracycline, and tylosin. Of these antibiotics, the β-lactam antibiotics, e.g. amoxicillin, ampicillin, cloxacillin, and penicillin are preferred, and penicillin is more preferred.

FIG. 1 shows the basic concept of the presently described invention, which is a method for removing contaminants, such as antibiotics, from a liquid food product that the contaminant can be found to adulterate. Special emphasis is placed on removing antibiotics from milk. An antibody 10 with a specific affinity for binding an antibiotic 12 is covalently attached to a solid support (matrix), such as a bead 14 made of glass, a ceramic material, or polystyrene to form an matrix-antibody composition 16, i.e. antibody-bead conjugate. The matrix-antibody composition 16 is then placed in contact with the antibiotic-adulterated milk 18 such that the antibody 10 contacts and binds the antibiotic 12 to form a complex 20. The antibody-antibiotic complex 20 is then separated from the milk to result in antibiotic-depleted or reconditioned milk 22 that can be sold and processed. Finally, the antibiotic 12 is removed from the antibody-antibiotic complex 20 to result in a regenerated matrix-antibody composition 24 that can be reused for removing antibiotics from milk.

A number of factors bear on the efficiency of the invention in removing contaminants from milk. These factors include the volume of milk to be treated, the number of antibodies bound to the solid matrix, the amount of solid matrix used to contact the milk, the temperature of the milk, the flow rate of the milk with respect to the antibodies, and the amount of time for the matrix to contact the milk. Therefore, as used herein, "effective amount" and similar terms are used to indicate an amount of matrix-antibody composition that is effective in removing the contaminant that is to be removed from the milk or other food product within a certain time. An effective amount is a function of the number of antibodies bound to the matrix, the quantity of matrix added per unit quantity of milk, temperature, time, steric factors, and perhaps other variables. For removing contaminants from milk, the temperature will be about 4±0.5° C., since milk must be held in this temperature range to comply with legal requirements, however the other factors can vary. The present invention is to be broadly construed to encompass variation in these other factors, thus the term "effective amount" is used.

Binding of Antibodies to Matrix

Antibodies used in the present description of the invention were purchased commercially. Polyclonal rabbit antibodies and monoclonal antibodies purified from mouse ascites fluid were purchased from American Qualex International, Inc. (La Mirada, Calif.). Polyclonal antibodies were produced against β-lactam and gentamicin antibiotics and were of the IgG$_1$ subclass. Monoclonal antibodies were IgG antibodies against β-lactam antibiotics. Both sets of antibodies react with all types of β-lactam antibiotics approved by the FDA for use in lactating dairy cattle. Antibodies could just as well be prepared according to methods that are well known in the art. E. Harlow & D. Lane, Antibodies: A Laboratory Manual (1988).

Antibodies were bound to glass beads according to the 3-step method of S. Bhatia et al., 178 Anal. Biochem. 408 (1989); Eigler et al., U.S. Pat. No. 5,077,210. First, the clean silica surface was coated with a silane film containing exposed thiol groups. The silanizing agent was mercaptomethyldimethylethoxysilane (MDS). Other silanizing agents having exposed thiol groups would also be suitable, such as 3-mercaptopropyltrimethoxysilane (MTS). Second, a heterobifunctional crosslinker having a thiol-reactive group and an amine-reactive group, N-γ-maleimidobutyryloxy succinimide ester (GMBS, Sigma Chemical, St. Louis, Mo.), was coupled to the thiol sulfur atom of the silane. The thiol group on the silane reacts specifically and covalently with the maleimide moiety of the GMBS crosslinker in organic solvent, leaving the succinimide moiety of the GMBS available for attachment to the antibody. Other heterobifunctional crosslinkers having a thiol-reactive group and an amino-reactive group that would also be suitable include N-succinimidyl-3-(2-pyridyldithio)propionate (SPDP), N-succinimidyl-(4-iodoacetyl)aminobenzoate (SIAB), and succinimidyl 4-(p-maleimidophenyl) butyrate (SMPB). Third, the succinimide moiety was bound to a terminal amino group of the antibody in aqueous solution to form a stable amide bond. These reactions are summarized by the following reaction scheme.

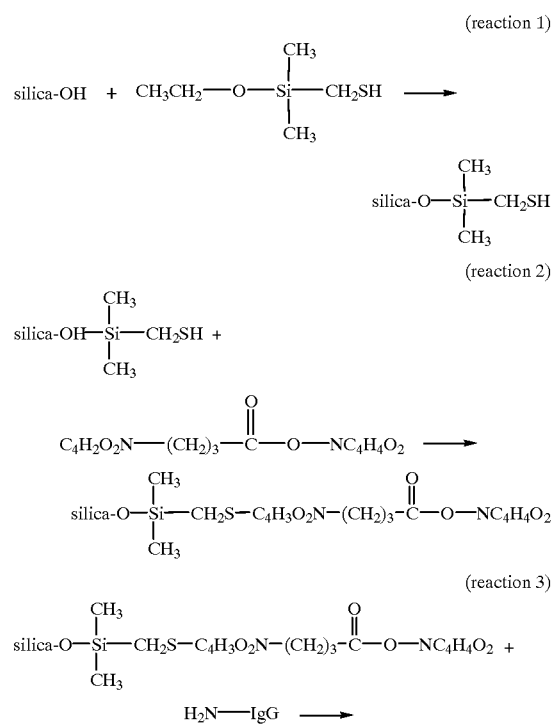

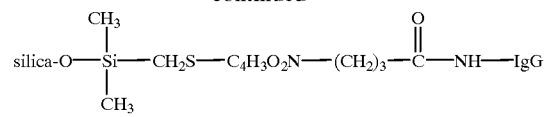

This method of forming a matrix-antibody composition results in the antibody being covalently bound to the solid support through an amino group of the antibody molecule. Such amino group can be the N-terminus of the light or heavy chains, or can be the amino group of a side chain on amino acids such as lysine, asparagine, or glutamine. A high proportion of antibodies attached to the matrix in this manner have both antigen binding sites available for binding an antigen. This method is thus distinguished from the nonspecific type of binding, often used in ELISA, wherein an antibody is attached to a solid support by means of an antigen binding site, thus leaving only one antigen binding site available for binding free antigen.

The procedure for attaching antibodies to the beads is as follows. Glass beads (5 mm diameter, nonporous) were purchased from Fisher Scientific (San Francisco, Calif., catalog no. 113126). Polystyrene beads (6 mm diameter, nonporous) were purchased from Rainin Instrument Co. (Emeryville, Calif., catalog no. 84-PSB-500). FDA-approved, food grade ceramic beads (5 mm diameter, nonporous) having a composition of 90% alumina oxide, 6.7% silica oxide, 2.5% magnesium oxide, and traces of six other oxides were from purchased from Coors Ceramic Co. (Golden, Colo., catalog no. 74502). The beads were acid-cleaned by immersion in a 1:1 mixture of concentrated hydrochloric acid and methanol for 30 minutes at room temperature followed by rinsing several times with distilled water. Next, the beads were treated with concentrated sulfuric acid for 30 minutes at room temperature, rinsed several times with distilled water, and autoclaved for 30 minutes in distilled water. Finally, the beads were placed on a piece of low lint tissue and allowed to air dry.

In a glove bag under an inert atmosphere, the beads were placed in a 2% solution of MDS in dry toluene for 2 hours. The beads were removed from the solution, rinsed in dry toluene, and allowed to air dry. Next, the GMBS was dissolved in a minimum amount of dimethylformamide and then diluted with absolute ethanol to a final concentration of 2 mM. The silanized beads were placed in the 2 mM GMBS solution for 1 hour and then removed and washed in PBS. Antibodies were bound by incubating a solution of 0.05 mg/ml of antibodies in PBS with the silane and crosslinker coated beads for 1 hour, after which the beads were washed with PBS.

An alternative method of immobilizing antibodies on beads involves use of beads containing reactive epoxide groups on the surface of the beads. These beads were obtained from Rainin Instrument Co., Inc. (Emeryville, Calif., catalog no. 84-QAB-250) and antibodies were attached thereto according to the manufacturer's instructions. Using this technique, each bead usually binds about 0.225 μg of protein. Briefly, the chemistry of the reaction involves nucleophilic addition of the antibodies to the epoxide groups on the beads through amino, hydroxyl, or sulfhydryl groups on the antibodies. This reaction is summarized by the following reaction scheme where X is a secondary amine, sulfhydryl, or hydroxyl.

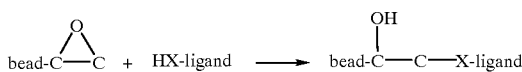

The ability of derivatized beads to bind antibodies was tested by placing one MDS/GMBS-derivatized glass bead in each of two vessels containing either $10^6$ anti-penicillin antibodies or $10^7$ anti-gentamicin antibodies in 200 µl of solution. The beads were incubated for 1 hour at room temperature, the beads were removed from the antibody solutions, and the antibody titers of the solutions were determined again. The titer of the anti-penicillin antibodies was about $10^5$ and that of the anti-gentamicin antibodies about $10^6$, demonstrating that about 1 log of antibodies was removed from each solution by incubation of the derivatized beads therein. Beads with antibodies bound thereto were then tested to determine their ability to bind and remove antibiotics from milk.

EXAMPLE 1

Penicillin G (Sigma, St. Louis, Mo.) was added to raw whole milk to concentrations ranging from 2 to 100 ppb. Each milk sample was then assayed for the presence of penicillin G with a commercially available detection kit, Cite Probe Beta-Lactam (IDEXX Corp., Portland, Me.). This detection kit has a limit of detection of 5 ppb for penicillin according to independent research conducted at Virginia Polytechnic Institute and State University. Milk and Dairy Beef Residue Prevention Protocol 44 (American Veterinary Medical Ass'n and Nat'l Milk Producers Fed. 1991). Then, one bead having bound anti-penicillin antibodies was placed into a 5 ml sample of each dilution of penicillin-containing milk. The bead and milk samples were incubated together at 4±0.5° C. for 30 minutes with gentle shaking at 50 rpm. The bead was removed from each sample and the milk samples were tested again with the Cite Probe kit. The results are shown in the table below.

TABLE 1

| Penicillin | Assay Results | |
|---|---|---|
| Concentration (ppb) | Before Treatment | After Treatment |
| $4.23 \times 10^6$ | + | ND |
| 100 | + | − |
| 75 | + | − |
| 50 | + | − |
| 25 | + | − |
| 10 | + | − |
| 8 | + | − |
| 5 | + | − |
| 2 | + | − |
| 0 | ND | − |
| $1 \times 10^5$ | ND | + |

ND Not done.

These results show that incubation of penicillin-contaminated milk with beads containing anti-penicillin antibodies can effectively remove the penicillin to levels below the level of detection at 4±0.5° C., the legally required holding temperature of milk during processing.

EXAMPLE 2

Milk from a farm where antibiotics had been administered to cows was treated according to the present invention to test the efficacy of removing antibiotics from milk in concentrations that might be encountered under actual conditions. Milk from cows treated with antibiotics was assayed by two methods prior to removal of the antibiotic with antibody-coated beads. One test was a standard disk assay where the diameter of a clearing zone around a sample-containing disk is proportional to the amount of antibiotic in the sample. Standard Methods for the Examination of Dairy Products (R. T. Marshall ed., 16th ed. 1992). The other assay was the Cite Probe assay described above. Each milk sample was then divided in two, and each half-sample of 20 to 40 ml was shaken at 70 rpm for 11 minutes at 4° C. with a single antibody-containing bead bound through either the MDS/GMBS system or epoxide system. After exposure to the bead, samples were assayed again with the Cite Probe assay. The results in Table 2 show that in milk from 4 of 5 antibiotic-treated cows the level of antibiotic in the milk could be reduced to below the level of detection under the conditions used. It is likely that the one sample that was still positive after treatment could have been rendered negative with additional incubation time.

TABLE 2

| | Pre-Treatment Assay | | Post-Treatment Assay | |
|---|---|---|---|---|
| Sample | Disk | Cite Probe | MDS | Epoxide |
| 7394 | Slight zone | + | − | − |
| 120/cow647 | 17 mm | + | − | − |
| 120/cow18 | 18 mm | + | − | − |
| 463/cow280 | 20 mm | + | + | + |
| 120/cow92 | 21 mm | + | − | − |

Under industrial conditions, the most important parameter for use of this invention is temperature, because of the legal requirement that milk be held at 4±0.5° C. during processing. Incubation time of the milk with the solid matrix having bound antibodies may be varied to account for differences in volume and concentrations of antibiotics from batch to batch. The format for application of the invention may be varied also, as is exemplified below.

EXAMPLE 3

Figure 2:
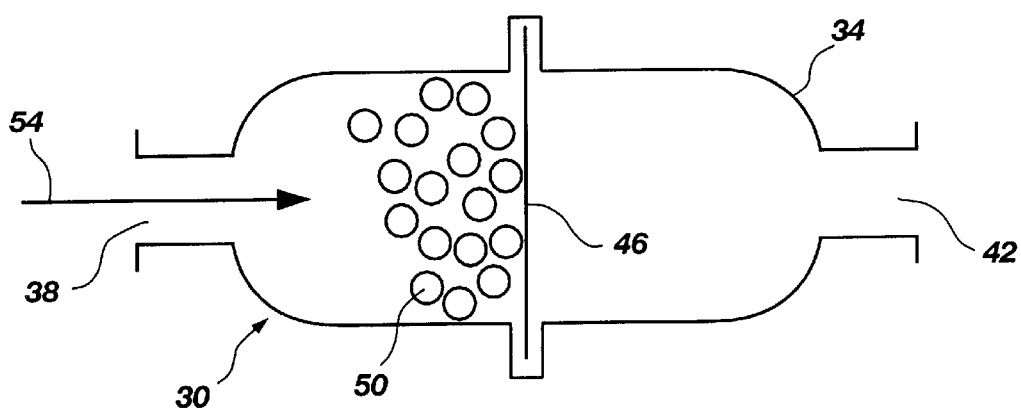
FIG. 2 is a schematic diagram of a flow cell for in-line removal of a contaminant from milk in a commercial dairy.

In this example, 7 mm beads (90 g) prepared according to the present invention were placed in a flow cell, i.e. fluidized bed cartridge, as shown in FIG. 2. The beads contained about 1000 anti-penicillin antibodies each. The flow cell 30 comprises a housing 34 having an opening 38 for flow of antibiotic-contaminated milk into the flow cell 30 and another opening 42 for flow of antibody-depleted milk out of the flow cell 30. A plate 46 having holes therein to permit flow of the milk through the flow cell 30 is place with the plane of the plate 46 generally perpendicular to the direction of flow of the milk. The beads 50 were placed upstream of the plate 46. Arrow 54 shows the direction of flow of milk through the flow cell 30. The size of the holes in the plate 46 was selected to be smaller than the size of the beads 50 such that the beads 50 could not pass through the holes and flow out of the flow cell 30 through the outflow opening 42. In this example, the holes were 3 mm in diameter. The housing 34 and plate 46 were constructed of stainless steel for durability and compatibility in a commercial dairy. The inflow opening 38 and outflow opening 42 were connected to 1.5 inch pipes.

Figure 3:
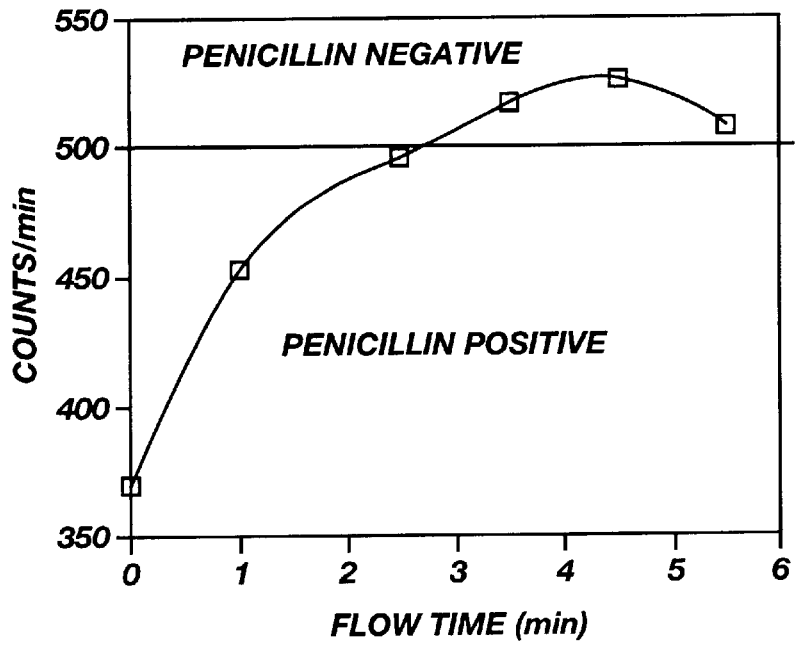
FIG. 3 is a graphic representation of removal of penicillin from raw, full fat milk with the flow cell of FIG. 2 at 100 liters/minute.

The flow cell 30 was placed in-line, and about 100 liters of raw, full fat milk contaminated with 100 ppb of penicillin was recirculated through the flow cell 30 at a rate of 100 liters/minute for 10 minutes. The temperature of the milk was 4±0.5° C. Samples were removed at 1 minute intervals and were assayed with the CHARM assay (Gossner Foods, Logan, Utah) for the presence of penicillin. The results, shown in FIG. 3, demonstrate that only 3–5 minutes were needed to remove the antibiotic to below the level of detection of the CHARM assay (1 ppb in milk). Thus, passage of the contaminated milk through the fluidized bed flow cell only about 3–5 times was sufficient to recondition the milk.

These results demonstrate that the instant method is effective in removing an antibiotic from milk under conditions found in a commercial dairy. The fluid bed cartridge is placed in-line with the flow of milk through the processing plant, and the milk is recirculated past the cartridge until the contaminant is removed and the milk is reconditioned. No special modifications are needed to the milk processing plant to accomplish this reconditioning, and the normal flow of milk through the plant is not restricted. This fluidized bed design is also advantageous because the cartridge is easily removed and replaced with a fresh cartridge when the antibodies are saturated with antigens.

The use of large beads (2–7 mm diameter) runs counter to the conventional wisdom that such large beads have insufficient surface area for binding significant amounts of antibody. For example, magnetic beads having diameters less than 2 μm are used for attaching antibodies in detection assays because of the large surface areas of such small beads. These beads are too small for use in the present invention, however, because they are not practical with flow rates of 100 liters/minute nor are the magnets strong enough to hold the antibodies in place due to the shear forces of the flow of liquid past the beads. It is therefore surprising that an antibiotic can be removed from milk in 3–5 minutes with large beads. Large beads are advantageous for packing in a fluidized bed and for high flow rates.

EXAMPLE 4

Figure 4:
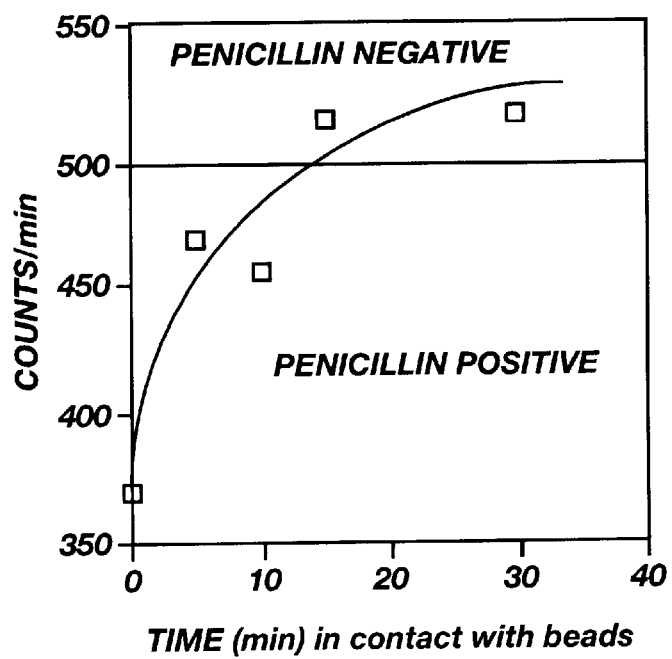
FIG. 4 is a graphic representation of removal of penicillin from raw, full fat milk containing a matrix-antibody composition with slow agitation.

In this example, 90 g of 7 mm beads prepared according to Example 1 were placed in 30 gallons of milk contaminated with 100 ppb of penicillin. The beads contained about 1000 anti-penicillin antibodies each. The milk and beads were slowly agitated for 30 minutes at 4±0.5° C., and samples were taken at 5 minute intervals for assay with the CHARM assay as in Example 3. The results, shown in FIG. 4, demonstrate that penicillin was removed to a nondetectable level (1 ppb) within 15 minutes. These results show that a batch method could be used to remove an antibiotic from milk. The complexed antibiotic would then be removed from the milk by filtration, sedimentation, or a similar method.

The amount of beads used was calculated on the assumption that only one antigen binding site would be available per antibody. After removal of the penicillin was complete, the matrix-antibody composition should have been saturated with antibiotic according to this calculation. Surprisingly, when more antibiotic was added, the beads were able to bind the additional penicillin. This observation suggests that the assumption that only 1 antigen binding site was available per directionally bound antibody was too conservative, and that in a high proportion of bound antibodies there were multiple antigen binding sites available for binding penicillin, as would be expected in directional attachment of antibody to matrix.

Other methods of practicing the invention are contemplated as within the scope of the invention, such as attaching the beads to ceramic membranes used for ultrafiltration or microfiltration and passing the milk through the membrane, or placing the beads in a porous bag and "floating" the beads in the milk until the antibiotic is removed.

EXAMPLE 5

In this example, the procedure of Example 3 is followed with the exception that the antibody in the matrix-antibody composition is specific for binding Bacillus spores.

EXAMPLE 6

Advantageously, the antigen-antibody complexes formed during removal of a contaminant from milk can be treated to release the bound contaminants so that the antibodies can be reused for removing contaminants from a liquid food product such as milk. One method for reactivating the antibodies is to incubate the complexes under high salt concentrations, such as in 0.5 to 1 M NaCl solution for 30 to 60 minutes at 25 to 37°. Many high ionic strength solutions would be equally effective, however NaCl is inexpensive, convenient, and relatively noncorrosive. Another method for reactivating the antibodies is incubating the matrix-bound antibodies at low pH. High ionic strength solutions are preferred over acid treatment, however, because of the relative convenience of handling concentrated salt solutions rather than acids.

I claim:

1. A method for removing a selected antibiotic from antibiotic-contaminated milk comprising the steps of:

(a) providing a matrix-antibody composition comprising an insoluble matrix having an antibody directionally attached thereto, said antibody having a specific affinity for binding said selected antibiotic; and (b) causing said antibiotic-contaminated milk to flow over said matrix-antibody composition at 4±0.5° C. a sufficient number of times for the antibiotic to form a complex with said matrix-antibody composition, thereby forming an antibiotic-depleted milk having an antibiotic concentration of less than 5 ppb.

2. The method of claim 1 wherein said antibiotic-depleted milk has an antibiotic concentration of less than 2 ppb.

3. The method of claim 2 wherein said antibiotic-depleted milk has an antibiotic concentration of less than 1 ppb.

4. The method of claim 1 wherein said antibiotic-contaminated milk is caused to flow over said matrix-antibody composition at a flow rate of up to 100 liters/minute.

5. The method of claim 1 wherein said antibiotic is a member selected from the group consisting of amoxicillin, ampicillin, bacitracin, ceftiofur, cephapirin, chlortetracycline, cloxacillin, dihydrostreptomycin, erythromycin, gentamicin, lincomycin, neomycin, novobiocin, oxytetracycline, penicillin, sulfachlorpyridazine, sulfadiazine, sulfadimethoxine, sulfamerazine, sulfamethazine, sulfamethizole, sulfanilamide, sulfapyridine, sulfathiazole, tetracycline, and tylosin.

6. The method of claim 5 wherein said antibiotic is a β-lactam antibiotic.

7. The method of claim 6 wherein said antibiotic is penicillin.

8. The method of claim 5 wherein said antibiotic is gentamicin.

9. The method of claim 1 wherein the matrix is selected from the group consisting of silicon, glass, silica, quartz, metal oxides, polyvinyl alcohol, polystyrene, and poly (acrylic acid).

10. The method of claim 9 wherein the matrix is selected from the group consisting of glass, metal oxides, and polystyrene.

11. The method of claim 10 wherein the matrix is in the form of a bead.

12. The method of claim 11 wherein said bead has a diameter in the range of about 2–7 mm.

13. The method of claim 1 wherein said matrix-antibody composition is contained in a fluid bed cartridge.

14. The method of claim 1 further comprising
   (c) removing said antibiotic from said complex so that said matrix-antibody composition is reusable.

15. The method of claim 14 wherein step (c) comprises incubating said complex in a high ionic strength solution.

16. The method of claim 15 wherein said high ionic strength solution comprises 0.5 to 1 M NaCl.

17. A method for removing a selected contaminant from contaminated milk comprising the steps of:
   (a) providing a matrix-antibody composition comprising an insoluble matrix having an antibody directionally attached thereto, said antibody having a specific affinity for binding said selected contaminant;
   (b) causing the contaminated milk to flow over said matrix-antibody composition at 4±0.5° C. a sufficient number of times for the selected contaminant to form a complex with said matrix-antibody composition, thereby forming a contaminant-depleted milk having a contaminant concentration of less than 5 ppb.

18. The method of claim 17 wherein said contaminant-depleted milk has an contaminant concentration of less than 2 ppb.

19. The method of claim 18 wherein said contaminant-depleted milk has an contaminant concentration of less than 1 ppb.

20. The method of claim 17 wherein said contaminated milk is caused to flow over said matrix-antibody composition at a flow rate of up to 100 liters/minute.

21. The method of claim 12 wherein said contaminant is selected from the group consisting of an antibiotic, a bacterial cell, a bacterial spore, a virus, a protein, and an enzyme.

22. The method of claim 21 wherein said contaminant is an antibiotic.

23. The method of claim 22 wherein said antibiotic is a member selected from the group consisting of amoxicillin, ampicillin, bacitracin, ceftiofur, cephapirin, chlortetracycline, cloxacillin, dihydrostreptomycin, erythromycin, gentamicin, lincomycin, neomycin, novobiocin, oxytetracycline, penicillin, sulfachlorpyridazine, sulfadiazine, sulfadimethoxine, sulfamerazine, sulfamethazine, sulfamethizole, sulfanilamide, sulfapyridine, sulfathiazole, tetracycline, and tylosin.

24. The method of claim 23 wherein said antibiotic is a β-lactam antibiotic.

25. The method of claim 24 wherein said antibiotic is penicillin.

26. The method of claim 23 wherein said antibiotic is gentamicin.

27. The method of claim 21 wherein said contaminant is a bacterial spore.

28. The method of claim 17 wherein the matrix is in the form of a bead.

29. The method of claim 28 wherein said bead has a diameter in the range of about 2–7 mm.

30. The method of claim 17 wherein said matrix-antibody composition is contained in a fluid bed cartridge.

31. The method of claim 17 further comprising
   (c) removing said contaminant from said complex so that said matrix-antibody composition is reusable.

32. The method of claim 31 wherein step (c) comprises incubating said complex in a high ionic strength solution.

33. The method of claim 32, wherein said high ionic strength solution comprises 0.5 to 1 M NaCl.

* * * * *